United States Patent [19]

Paré

[11] Patent Number: 5,338,557
[45] Date of Patent: * Aug. 16, 1994

[54] MICROWAVE EXTRACTION OF VOLATILE OILS

[75] Inventor: J. R. Jocelyn Paré, Gloucester, Canada

[73] Assignee: Her Majesty the Queen in right of Canada, as represented by the Minister of the Environment, Ottawa, Canada

[*] Notice: The portion of the term of this patent subsequent to Mar. 26, 2008 has been disclaimed.

[21] Appl. No.: 29,358

[22] Filed: Mar. 10, 1993

Related U.S. Application Data

[63] Continuation-in-part of Ser. No. 670,769, Mar. 18, 1991, abandoned, which is a continuation-in-part of Ser. No. 519,588, May 7, 1990, Pat. No. 5,002,784.

[30] Foreign Application Priority Data

May 16, 1989 [CA] Canada ................... 600322

[51] Int. Cl.⁵ .............................................. A23L 1/00
[52] U.S. Cl. ..................................... 426/241; 426/430
[58] Field of Search ................. 426/241, 428, 429, 430

[56] References Cited

U.S. PATENT DOCUMENTS

| | | | |
|---|---|---|---|
| 2,925,328 | 2/1960 | Romagnan | 422/128 |
| 3,870,053 | 3/1975 | Heitkamp et al. | 426/241 |
| 4,400,398 | 8/1983 | Coenen et al. | 426/430 |
| 4,464,402 | 8/1984 | Gannon | 426/242 |
| 4,554,132 | 11/1985 | Collins | 422/68 |
| 4,673,560 | 6/1987 | Masse et al. | 423/532 |

FOREIGN PATENT DOCUMENTS

| | | |
|---|---|---|
| 578313 | 10/1986 | Australia . |
| 1209675 | 10/1970 | United Kingdom . |
| 2004197 | 3/1979 | United Kingdom . |

OTHER PUBLICATIONS

Ganzler et al, Journal of Chromatography (1986), pp. 299-306.
Ganzler et al, F. Lebensm Unters Forsch (1987), pp. 274-276.
Craveiro et al, Flavor and Fragrance Journal, vol. 4, pp. 43-44 (1989).

*Primary Examiner*—George Yeung
*Attorney, Agent, or Firm*—McFadden, Fincham

[57] ABSTRACT

There is disclosed a method and apparatus for extraction of essential and other such oils from plant and animal biological matter by exposure to microwave energy. The method involves exposure of microwaves to the oil containing cellular matter of the glandular system to extract the oil into a suitable non-aqueous organic medium after disruption of the oil containing cellular matter. The apparatus includes microwave applicators, solvent and starting material, storage means and multiple stages of treatment resulting in a high quality extracted product.

12 Claims, 1 Drawing Sheet

MICROWAVE EXTRACTION OF VOLATILE OILS

This application is a continuation-in-part of Ser. No. 07/670,769 filed Mar. 18, 1991, which is a continuation-in-part of Ser. No. 07/519,588 filed May 7, 1990 now U.S. Pat. No. 5,002,784.

BACKGROUND OF THE INVENTION

1. Field of the Invention

This invention relates to a method of extracting soluble natural products from biological matter using microwave energy and apparatus therefor.

2. Description of the Prior Art

Various microwave advances have been documented where e.g. grains containing fats and oils have been dried by microwave heating, followed by steps to remove husks and to extract oils, e.g. U.S. Pat. No. 4,464,402 Gannon. Grains and seeds also have been microwave treated to heat the extracted medium, e.g. Ganzler and Salgo, 1987, Z. Lebensm Unters Forsch 184: 274–276. In these experiments, radiation was primarily employed to heat the extractant medium.

Microwave drying of food products followed by subsequent solvent extraction is disclosed in U.S. Pat. No. 4,554,132 by Collins, but with no extraction process.

British 1,209,675 discloses inactivating enzymes of palm fruits with microwave radiation, followed by solvent extraction of palm oil.

Heitkamp et al., Canadian 987,993, describes a microwave induced migration of flavour and aroma constituents towards the surface in certain tissue such as tobacco or tea in the presence of moisture and optionally a solvent. Heitkamp does not teach any enhanced extraction of the flavour or aroma constituents into the extracted medium.

Additionally, Craveiro et al. in the *Flavour and Fragrance Journal* 4., 1989: 43–44, discuss the production of volatile material from plant material exposed to microwave energy in an air stream.

Ganzler, Salgo, and Valko in *Journal of Chromatography*, 371, 1986: 299–306, disclose microwave sample preparation organophosphate pesticides, antinutritives and crude fat samples. Dried sample materials are milled to the point of particulation and suspended in an organic medium. The Ganzler et al. method describes an extraction in which the glandular and vascular matter of the dried sample material is destroyed mechanically prior to microwave treatment; this causes a loss of volatile oils and allows for undesirable materials to be obtained. That method calls for a long centrifugation time, a well-known extraction technique- In addition, the method indicates that the suspensions of samples and solvents are cooled and subsequently re-exposed to microwaves. Thus, heating of the extraction environment occurs with no recovery of the extractant or any volatile oils.

Steam distillation and solvent extraction methods are well known in the art but are limited by high temperatures, as well as being dangerous when using certain organic solvents and being deficient in producing an uncontaminated product.

Accordingly, there is a need for an extraction method and apparatus for producing maximum yields and recovery of volatile oils and other useful substances contained in cellular biological material by microwave inducement without any of the disadvantages and inherent limitations of the prior art.

SUMMARY OF THE INVENTION

With the present invention, an extraction protocol for various natural products is provided, without being limited to, human usage, e.g. ingestion or topical application, without the hazards associated with conventional extraction techniques and which is more selective, efficient and rapid.

The present invention employs microwave energy to generate a sudden temperature increase in the glandular and sometimes vascular systems of biological material, contacted with an appropriate quantity of a suitable non-aqueous organic solvent or extractant as defined hereinafter.

One aspect of the present invention provides a method of obtaining volatile oils from biological material containing such volatile oils comprising the steps of providing a source of biological material having a substantially intact glandular system, the biological material having a moisture content sufficient to permit the extraction of the volatile oils by microwave energy. In the method, the biological material is surrounded with a non-aqueous extractant for the volatile oils. Then, the biological material is exposed to a microwave energy source to effect differential heating between the biological material and the non-aqueous extractant to thereby express the volatile oils from the biological material while cooling the expressed volatile oils from the biological material with the non-aqueous extractant to a temperature below the temperature at which the expressed volatile oils are extracted from the biological material. The process may include separating residual biological material from the extracted oil in the solvent and recovering the oil.

A particularly advantageous method involves immersing a source of biological material having cellular matter containing the oils in a non-aqueous organic extractant, the source of material having a substantially intact glandular system and a moisture content sufficient to rupture the glandular system under microwave treatment. Thereafter, the source material is exposed to a microwave energy source to elevate the temperature of the biological material to a degree sufficient to rupture the glandular system and express the volatile oil from the biological material into the organic extractant.

Following recovery of the volatile oil in the organic extractant, in a first extraction step, the volatile oils extracted from the biological material are cooled with the non-aqueous organic extractant. Further, an additional source of the biological material is added to the resulting extractant, containing extracted volatile oils from the first extraction step, and exposed so that the combined biological material and the resulting extractant is treated with a microwave energy source sufficient to elevate the temperature of the biological material to rupture the glandular system of the biological material contained in the resulting extractant to express and disperse volatile oil therefrom. This may be repeated several times. In the next step, the volatile oils are separated from the further extractant thus obtained.

In accordance with a still further aspect of the present invention, there is provided a further process for extracting soluble products from biological material comprising:

(a) subdividing a biological feed material into subdivided material;

(b) contacting the subdivided material with an extractant which is transparent or partially transparent to microwave radiation;

(c) exposing the subdivided material, while in contact with sufficient extractant to enable extraction to occur, to a microwave energy source to effect differential heating between the biological material and the non-aqueous extractant to thereby express the volatile oils from the biological material and cooling the expressed volatile oils from the biological material with the non-aqueous extractant to a temperature below the temperature at which the expressed volatile oils are extracted from the biological material; and (d) separating the residual material from the extractant phase.

In a particularly advantageous embodiment, concentrated extracts of the volatile oils can be obtained upon reducing the amount of solvent normally required for that purpose. Thus, where an extractant is used repeatedly, solvent usage is reduced resulting in a more economical and valuable operation.

In contrast to other procedures, this invention causes the microwave energy to be absorbed by the material being treated in a preferential manner, compared to the solvent, so that oils expressed from the biological material are then immediately cooled by the surrounding solvent, thus avoiding exposure of the oils and sensitive materials to heat degradation by the microwave treatment of the biological material.

Therefore, Applicant's process is a "cool process" in which the solvent medium does not heat up due to absorption by the solvent of microwave energy and substantially all of the microwave energy used is imparted to the material being treated. The positive differential in temperature between the biological material and the extract ensures that the oil migrates towards the extractant.

The extractant may be selected from suitable organic solvents known to those skilled in the art, for example, alkanes e.g. hexane or other such suitable non-aqueous aliphatic organics. Generally, such materials are termed "microwave transparent", i.e. they do not heat or there is no significant microwave energy absorption upon exposure due to the lack of a molecular dipole moment. Thus, cooling of the extracted oils from cellular biological material occurs. Co-solvents may also be employed. The extractants should have a static dielectric constant of between about 0 to 28, or should be transparent to the microwave frequency of the microwave source.

In the case where the biological material is substantially devoid of any moisture, rehydration or resolvation of the material may be achieved, prior to microwave treatment, by incorporating a solvent which is not transparent to microwaves, i.e., those having a net dipole moment. These solvents include, for example, methanol, ethanol and mixtures of solvents, etc.

In the event that a partially transparent organic solvent is used, the temperature of the same remains below that of the biological material and more specifically, the extracted oil, during a microwave treatment. This ensures that the oil containing matter will be cooled. It will also ensure the migration of the oil into the extractant.

Another aspect of the invention employs an extraction media system either as a single extractant or a solution of two or more suitable and compatible extractants, in series, to obtain fractionated oil extractions.

Applicant has found that by utilizing non-particulated material as the material to be treated, superior results are obtained; the prior art has proposed utilizing finely ground or particulated dried material which results in substantial non-selective alteration of glandular and vascular tissues which is, of course, a primary necessity for volatile oil extraction. By using substantially whole or large pieces of material, destruction of glandular and vascular systems is avoided resulting in higher and more valuable extraction of desired products.

Glandular tissue, as used herein, refers to those organs responsible for various secretions i.e. nectary secretions. Vascular tissue refers to channels for the conveyance of fluids. Generally, the volatile oils for extraction from biological material include the essential oils located in the glandular system. Such oils carry the essential odour or flavour of the biological material and are used in perfumes and flavourings. As is known, the volatiles, i.e. essential oils, are distinguished from the fixed oils e.g. cottonseed, linseed or coconut oils etc. in that the former oils are not glycerides of fatty acids.

As used herein, the term "volatile oils" includes not only those substances derived from plant and animal materials such as essential oils, but also substances such as lipids, fatty oils, fatty acids, etc. which, while not having the same degree of volatility as essential oils, are expressed or "volatilized" from the glandular or like system of such plant and animal materials, by the process described herein.

The present invention is applicable to many types of tissue e.g. plant material for flavouring and fragrance purposes, and other tissues e.g. animal tissue. Examples of plant material include Canadian pepper mint, seaweeds such as Irish moss, microalgaes, various types of vegetables, e.g. onions, garlic and the like. In the case of animal tissue, liver, kidney, egg yolk, etc. or animal products e.g. sea anemones, sea cucumber and crustaceous products (e.g. lobster or other shell fish), warm and cold water fish (e.g. trout, etc.) can be employed to extract pigments, oils, etc. Other biological materials that may be used include bacterial cultures, cell cultures, tissue cultures, yeasts, fermentation broths, and any resulting biomass materials from such cultures or the like. One preferred application relates to the extraction of the desirable oils from fish components such as the liver which are a source of desirable acids for pharmaceutical and human purposes e.g. volatile oils such as omega-3 and omega-6 oils and the like and the resulting biomasses therefrom.

The present invention also provides an apparatus for the extraction of essences and other substances from biological material, comprising at least one microwave applicator and includes means for feeding a mixture of biological material and an extractant through the microwave applicator for treatment. Further, means are provided for separating liquid from the treated mixture and removing the extractant from the filtered liquid.

The microwave applicator may operate within available known parameters e.g. a power rating of about 200 to 10,000 Watts and a frequency range of within about 2,000 to 30,000 MHz. Any wavelength within the microwave spectrum which is absorbed to some extent by a component of the material, can be used as only minor changes in the irradiation time are necessary to compensate for changes in absorption. Several such apparatus applicators may be provided in parallel for exposure of the biological material thereby.

The apparatus provides a solvent reservoir of suitable material compatible with the organic solvents, and solvent inlet and sample inlet means. The mixture is fed into or through the applicator by a suitable means e.g. a pump and is subsequently passed into the filtering means e.g. filter paper stages, Teflon (TM) screening etc. for removal of residual plant material. In addition, the apparatus may include means for removing any water content derived from samples being treated; such means may include, e.g. suitable desiccants for this purpose which may be incorporated as a separate stage or into, e.g. the filtering means.

The material is preferably pumped to a separator e.g. a rotary vaporizer etc. for separation of the solvent from the oil material. The solvent may, additionally, be passed through a condenser such as those known in the art, for condensing the solvent.

Those skilled in the art will appreciate that the "passing" of the material mentioned herein is achieved through the use of suitable connecting lines e.g. glass tubing, Teflon (TM), quartz or other microwave transparent equipment for microwave treatment. In addition, the lines include suitable valves, e.g. glass or Teflon stopcocks etc.

BRIEF DESCRIPTION OF THE DRAWING

Having thus generally described the invention, reference will now be made to the accompanying drawing, illustrating a preferred embodiment.

Figure 1:
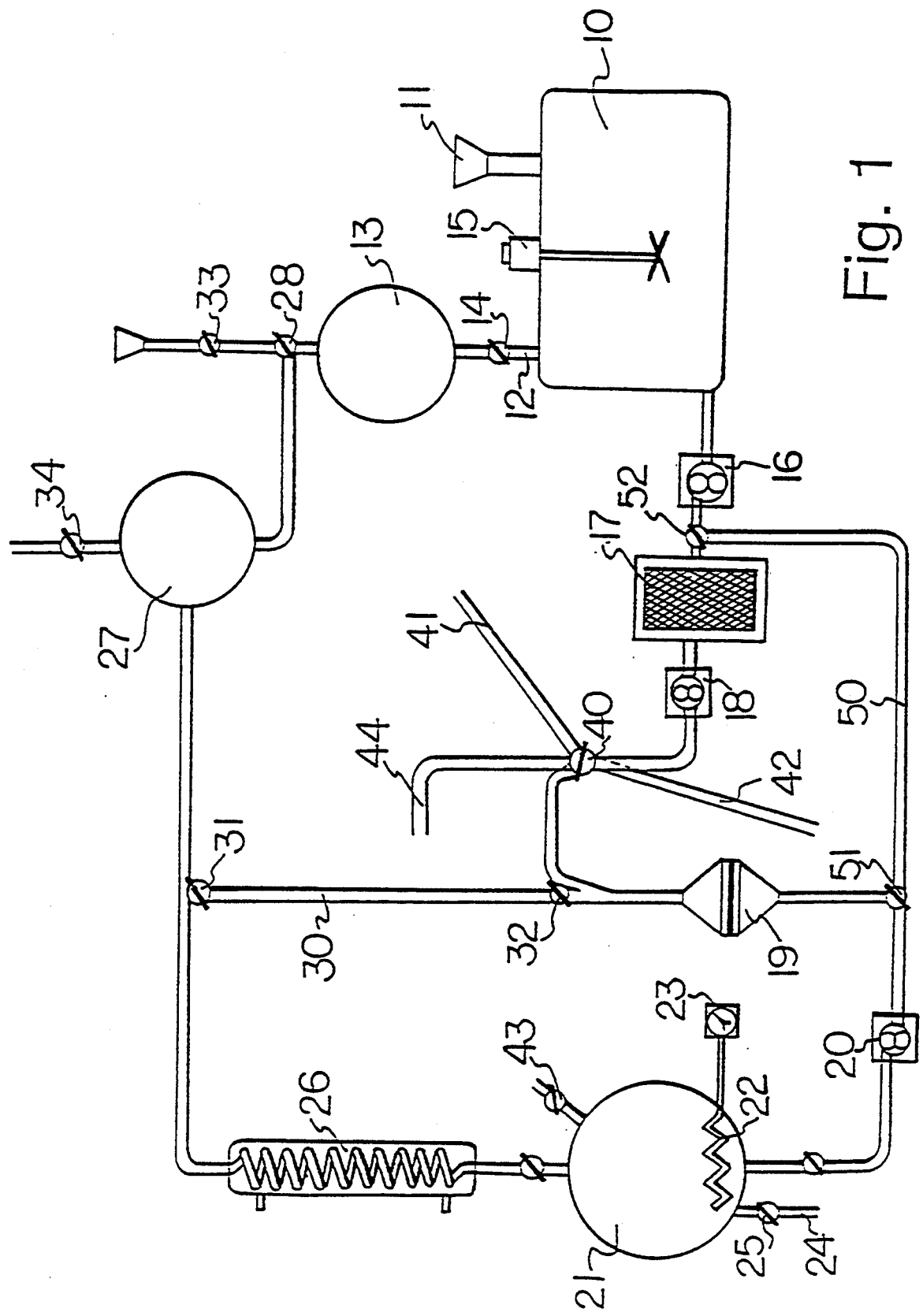
FIG. 1 is a diagrammatic representation of the apparatus of the present invention.

With respect to the method, the microwave irradiation process generally proceeds as follows: the microwave rays travel freely through the microwave-transparent extraction medium and are allowed to reach the inner glandular and vascular systems of the biological material [a microwave transparent medium can be defined as a medium that does not possess a significant static dielectric constant i.e. net dipole moments, e.g. hexane (1.9), carbon tetrachloride (2.2), and liquid $CO_2$ (1.6 at 0° C. and 50 atm.) as opposed to large dielectric constant substances, e.g. water (80.4)]. A subdivided portion of these microwave rays is absorbed by the biological material; the absorption efficiency is largely related to the moisture content (or added absorbing component) of the material at the time the extraction process is carried out. The result is a sudden rise in temperature inside the material which is more pronounced in the glandular and the vascular system. The temperature keeps rising until the internal pressure exceeds the capacity of expansion of the cell walls thus creating an explosion at the cell level. Substances located in the cells are free to flow out of the cells migrating to the surrounding medium that is cool and traps and dissolves the oils. The solid biological material can be removed, e.g. filtered-off with the resulting solution being processed in the same manner as any other natural product extract.

The extractant amount used to contact or submerse the feed material can vary widely, normally sufficient to extract substantially all of the desired components to totally physically cover the biological material. The ratio of extractant to feed material (L/kg) can be e.g. about 1:1 to about 20:1.

Electron micrograph examination of freshly extracted plant material reveals that the degree of disruption in the internal structure of the gland system of, e.g. Canadian pepper mint, is as large for a 20-second microwave-induced extraction as it is for conventional 2-hour steam distillation and for 6-hour Soxhlet extraction processes. Electron micrographs also provide an explanation for the superior quality of the extracts obtained as the relatively short period of extraction e.g. 2 to 3 minutes can be varied so that the penetration power based on the extraction medium can be controlled. In the case of an essential oil from pepper mint, using e.g. hexane as solvent, the short extraction period combined with the use of non-particulated fresh material prevents pigments and other undesirable components that are located within the plant to be accessed by the extractant. Macerated material is used in conventional steam distillation and other extraction processes where the final mesh size is very critical, and implies an extra step, compared to this invention. Direct visual examination corroborates this phenomenon as extracts obtained by this invention are far less pigmented than steam distillation counterparts.

This invention permits the possibility of using a system of extraction media, whether as a single extractant or a solution of two or more extractants, also in series, in order to obtain fractionated extracts in a matter of minutes and making use of the same equipment. Current technology requires separate distillation processes that are costly and time consuming. Different and extensive instrumentation is also required, resulting in a much larger capital investment. This invention enables a producer to perform a series of extraction and fractionation processes at the same site, using the same equipment, in less time than is required by current technology.

The period of time necessary to irradiate the material to extract the oils with microwave rays varies with the variety of the plant or other biological material; typical times being from about 10 to 100 seconds. Irradiation times also vary with the moisture content of the feed material since water is very efficient at absorbing microwave rays. The moisture content of the material should be from about 25% to about 90%. This extraction method can be used for batch processes as well as for continuous processes.

The extraction product may be recovered from the extractant (after separation from the residual solid plant material as by screening, filtering or centrifuging) if desired by distillation, reverse osmosis, preferential extraction, chromatography, etc. Suitable recovery techniques are known to those skilled in the art. The depleted extractant phase may be recycled without further purification.

Reference will now be made to the examples of the invention provided below wherein microwave radiation-induced extraction was used. Disruption of the glandular and vascular systems of a variety of materials, as in the particular manner described herein, demonstrate the improvements. These include, for example, yield, quality of the extract, reduced time and production costs (reduced personnel costs and reduced operational costs), reduced raw material costs (because of reduced raw material preparation costs), reduced number of operations, and reduced process-related hazards (to humans and to facilities), or a combination thereof, over the conventional extraction processes. These examples are illustrative and typical, but not exhaustive or limiting.

EXAMPLE 1

For comparative purposes, the essential oil of pepper mint (*Mentha piperita*) was obtained by a 2 hr. steam distillation yields of about 0.3% based on finely ground freshly harvested plant tissue (two particular steam distillation experiments gave yields of 0.264% and 0.290%).

For the purpose of this invention, freshly harvested mint plant tissue was formed into non-particulated pieces about 1 cm in size thus leaving most of the glandular cells intact. Three 100 g samples were each placed into open vessels into which 250 ml of microwave-transparent hexane at room temperature was poured thereby immersing the material. These samples were subjected to microwave exposure to establish differential heating between the microwave-transparent hexane and the glandular cells of the mint plant tissue. The period of exposure was 40 seconds applied at 625 Watts and at a frequency of 2450 MHz. The glandular cells, as a result of the exposure, ruptured and dispersed the oils contained therein into the hexane for cooling. The residual mint tissue was then removed on a coarse filter paper and the mint oil extracted into the hexane was subsequently recovered from the hexane by evaporation in vacuum. The mint plant material produced an oil at comparable yields to steam distillation for 2 hrs. Three microwave extraction experiments resulted in yields of 0.474%, 0.343% and 0.296%; the yields being dependent upon the residual moisture content of the feed material which, in this case, was 80% by weight.

The quality of the microwave extracts obtained by Example was superior to the steam distillation extract, as evidenced by the lower percentage of pulegone and higher percentages of menthol and menthone; a sales revenue weighted factor was used to demonstrate (Table I) the economic advantages of this invention. While the microwave-extracted oil was of a higher grade (and higher market value) this was ignored in the cost comparison in Table I, where it is evident that the net revenue factor (or difference between cost and expected sales revenue) was almost twice that of conventional steam distillation. In other words, Table I shows that the use of this invention would lead, in this particular case, to a net profit 94% greater than the results of the current steam distillation process.

TABLE I

| Factor | Conventional Steam Distillation | Microwave Process |
| --- | --- | --- |
| Revenues from sales | 1.00 | 1.00 |
| Purchasing of raw materials | 0.46 | 0.46 |
| Processing costs | 0.24 | 0.13 |
| Manpower costs | 0.11 | 0.055 |
| Containers and labelling | 0.0075 | 0.0075 |
| Net revenue factor | 0.18 | 0.35 |

EXAMPLE 2

Example 2 presents specific data of another plant material, with respect to the changed nature of the extract contents, compared to steam distillation extracts.

Sea parsley, having a 90% moisture content, obtained in Canada, was cut into pieces about 2.5 cm so that the glandular system was substantially intact. Samples of 100 g of similarly chopped material having an 80% moisture content were immersed in 250 ml hexane and subjected to microwave energy (power 625 watts, frequency 2450 MHz) for 40, 50 or 60 seconds.

Comparative samples of the chopped material (90% moisture) were subjected to steam distillation for 90 min. The percentage of oil steam distilled or extracted into hexane was then calculated. Apiole, an important constituent, was determined in the feed and in the extracted oil by gas chromatography. Results are given in Table II.

The market value of sea parsley essential oil is highly dependent upon apiole content. Table II shows the superior contents of apiole in the essential oil obtained by this invention compared to steam distillation.

TABLE II

| Process | % apiole in feed | % oil extracted | % apiole in oil |
| --- | --- | --- | --- |
| Steam distillation (90 min; 1" pieces) | 0.151 | 0.225 | 67.1 |
| Steam distillation (90 min; macerated) | 0.139 | 0.210 | 66.3 |
| Microwave irradiation (40 s; in hexane) | 0.130 | 0.165 | 78.8 |
| Microwave irradiation (50 s; in hexane) | 0.136 | 0.180 | 75.6 |
| Microwave irradiation (60 s; in hexane) | 0.121 | 0.161 | 75.2 |

Table II also shows that use of this invention led to a somewhat smaller (by 25%) essential oil extract size, but the quality of which, as determined by its apiole contents, was greater (by 15%). Furthermore, the microwave extraction results of Table II were carried out with sea parsley containing only 80% of residual moisture, whereas the steam distillation experiments were performed with material containing 90% residual moisture content. The material for microwave extraction was less costly to acquire because of its reduced cost (sold on a per weight basis) and its reduced apiole contents (as water evaporated off it carried apiole with it). It is noteworthy that the microwave extraction process not only provided a better apiole extraction yield, but it did so with plant material that had a reduced apiole starting content. This clearly shows the net "value added" obtained when employing this invention. The result is that a relatively larger net revenue (due to the combination of the two factors, namely reduced raw material supply cost and higher priced extract, exceeding the reduced production factor) is obtained by the present invention.

EXAMPLE 3

Steam distillation of cedar (*Thuja occidentalis*) produces an essential oil that suffers from its elevated content of less volatile components. To remedy this, it is necessary to shorten the extraction process time or to proceed with a subsequent fractionated distillation process. The former implies costly reduced yields whereas the latter is indicative of higher production costs and a more than doubled production time. This invention can be used to alleviate these problems in a manner whereby two fractions can be obtained, in an overall production time that is still less than the time required to proceed to single steam distillation product. Furthermore, the light or hexane fraction obtained by this two-stage extraction had a higher market value compared to the steam distillation extract since it was cleaner in terms of having less of heavy, undesired components.

Table III depicts these features from tests where fresh cedar material was subjected to a 2 hr. conventional steam distillation process in one experiment; or to two 30 sec microwave irradiation treatments, in series, on the same material, one treatment while immersed in ethanol and the other while immersed in hexane. The data in Table III are normalized with respect to the ten most important constituents of a steam distilled essential oil sample taken as determined from a gas chromatographic separation procedure (on a fused silica column of type DB-5 with appropriate temperature programmation). This GC procedure is the usual means of evaluating the contents of a given essential oil. The power of the second microwave treatment was reduced to 312.5 watts (from 625 watts) for hexane extraction to further reduce the processing costs and to take into account that the vascular system of the plant material had already been disrupted in the first microwave treatment. It has been found in other tests that proceeding to a steam distillation on material that had already been subjected to microwave irradiation, while immersed in ethanol, led to an extract of similar contents to that of the hexane extract described in Table III, i.e. devoid of its heavy fraction contents.

TABLE III

| Extraction Conditions | 10 Most Important Components of Cedar Essential Oils (%) | | | | | | | | | |
|---|---|---|---|---|---|---|---|---|---|---|
| | 1 | 2 | 3 | 4 | 5 | 6 | 7 | 8 | 9 | 10 |
| Steam distillation | 2.02 | 15.9 | 61.3 | 10.9 | 3.05 | 1.86 | 1.93 | 0.92 | 0.97 | 1.26 |
| Microwave: | | | | | | | | | | |
| Ethanolic extract | 0 | 0 | 3.15 | 0 | 0 | 0 | 0 | 0 | 39.6 | 54.3 |
| Hexane extract | 2.63 | 14.1 | 59.7 | 11.1 | 3.68 | 0 | 5.03 | 3.85 | 0 | 0 |

A sequential use of microwave treatments with a combination of solvents or solvent systems yields, in this particular example, a higher market value essential oil (hexane extract) because of its greater cleanliness, i.e. lack of contaminants, when compared to conventional steam distillation products, since the hexane extract was devoid of undesired heavier fractions removed in the ethanolic extracts. The microwave-induced ethanolic extract, obtained in this first microwave treatment, can be used in the same manner as fractions that are obtained by more tedious, costly fractionated distillation processes, e.g. "as is" in oleoresin formulations. As in the previous examples, both ethanol and hexane in these microwave extractions remained cool with respect to the plant material due to the differential heating, thus expressing a high content of oil into the hexane and ethanol. A further advantageous consequence of this is that the main fire and explosion hazards and the special ventilation requirements concomitant with conventional extraction techniques employing inflammable and/or volatile solvents, are substantially reduced.

EXAMPLE 4

It is well recognized that some natural product extracts are highly sensitive to heat treatment because of the high lability of its contents. Garlic suffers heavily from this phenomenon which represents a major hurdle to the production of an extract of reproducible quality that can satisfy the consumers' demand for uniformity. It has been shown in the literature that a large fraction of garlic extracts known to date consist of artefacts produced during the heat-derived extraction scheme. Steam distillation, although considered a relatively mild heat treatment, suffers from the same pitfalls, i.e. leads to similar artefacts being produced. Throughout the microwave-induced extraction of this example, the garlic system remained close to ambient temperature.

Garlic, having a 30% moisture content, was chopped to a size of about 1 cm and 100 g samples were immersed in 250 ml of dichloromethane. Samples of the chopped material were subjected to steam distillation for 2 hrs. Samples in dichloromethane were subjected to microwave (625 watts, 2450 MHz) for 30 seconds and similar to the previous examples, the dichloromethane was cool with respect to the garlic sample. The oil extract was recovered by vacuum evaporation and analyzed for its components by gas chromatography.

Table IV shows that the contents of the microwave-induced extract possessed two unreported sulphur-containing compounds B and C. The relative yields obtained for these two compounds were very reproducible from one experiment to another.

TABLE IV

| Composition of Garlic Extracts (%) | | | | | | | | | | |
|---|---|---|---|---|---|---|---|---|---|---|
| Microwave Irradiation (30 sec; in CH$_2$Cl$_2$) | | | Steam Distillation (2 hr) | | | | | | | |
| A* | B | C | A* | D | E | F | G | H | I | J |
| 22.2 | 28.4 | 49.4 | 14.7 | 5.80 | 45.9 | 9.92 | 8.96 | 4.84 | 5.96 | 3.94 |

*Component A is the only component that is common to both extracts.

Results typified by Table IV, show that the use of this invention led to a stable garlic extract consisting primarily of natural products B and C, that are not process related artefacts since they were reproducible and not altered by changed conditions (as is the case for garlic extracts obtained from conventional extraction procedures). The ratio of components B/C of the microwave irradiated extracts was reproducible within 0.5% in repeated tests. Component A, that is also found in steam distillation extracts varied more; thus it might be a process related artefact as well. All components in the steam distillation extracts varied widely (over 10%) between samples that were produced at the same time and with the same extraction conditions. It is apparent from the data that the process according to the present invention leads, in some cases, to the development of novel more reproducible ingredients for the food, feed and pharmaceutical industries, that were not extractable with any previously known extraction procedures.

EXAMPLE 5

*Monarda fistulosa*, a novel species of *Monarda* is a new product for perfumery and flavouring starting materials. It produces much higher concentration of geraniol in its essential oil than other genera within the *Monarda*. For comparative purposes, the essential oil of *Monarda fistulosa* was obtained by this method. In this example, 30 g of the fresh plant material were torn into fairly large pieces (same lot as for steam distillation) and placed in a 400 mL beaker and immersed in 175 mL of hexane and the temperature of the mixture was recorded; the mixture was submitted to a 15-second microwave irradiation period (of 500W and at 2450MHz) and the temperature of the medium was again recorded; this last step was repeated twice without taking further temperature measurements (i.e. a total of 45 seconds of microwave irradiation was applied and a total of 4 temperature measurements were taken). The data indicate that the internal temperature of the plant material became elevated during the exposure to thereby establish the required temperature gradient necessary for high extraction efficiency of the oils, etc. into the cooler hexane medium, (temperatures of only 15°, 29°, 44° and 57° C. were reached by passive heat conduction from the plant material for microwave exposure period of 0, 15, 30 and 45 seconds, respectively). The yield was found to be 1.49%.

The cellular temperature of the plant material is high, i.e. of the order of 100° C. owing to moisture content, and the intracellular moisture diffuses into the hexane medium to cause a slight temperature change, however this temperature is low in comparison to the oil material and therefore did not affect the temperature gradient to any appreciable extent evident from the extraction data.

Subsequent to the mixture of the oils and extractant medium cooling, the mixture was then filtered over a small quantity of sodium sulphate (to remove traces of water) and washed with 50mL of fresh hexane. The extract was reduced, the yield was determined and the extract was analyzed by gas chromatography coupled to a mass selective detector (the mass spectral data being compared to a library of standards). The data are summarized in Table V.

The same microwave-assisted experiment was repeated as per above until the last filtration step. At that point, instead of reducing the extract, the extract is used as an extraction medium to perform two other sets of experiments, i.e. a total of 90g of plant material is extracted (in three lots of 30g, each being submitted to three irradiation sequences of 15 seconds) in a single aliquot of hexane. The total extraction was then filtered (over a small quantity of sodium sulphate), rinsed with another 50mL of fresh hexane and reduced. The yield was determined and the contents were analyzed under the same conditions as per above. The yield (1.54%) and the sample contents proved to be identical to those noted above within the experimental error. Table V summarizes the analytical results and shows that, again, the microwave-assisted extract was of greater commercial market value by virtue of its enhanced contents in geraniol.

TABLE V

| Component | Relative Concentration | |
|---|---|---|
| Distillation | Microwave process | Steam |
| Octen-3-ol | 0.23 | 0.28 |
| Myrcene | — | 0.59 |
| p-Cymene | — | 0.12 |
| α-Terpinene | 0.21 | 0.96 |
| Linalool | 0.37 | 0.62 |
| Nerol | 0.57 | 0.33 |
| Geraniol | 98.48 | 94.83 |
| Germacreen D | 0.14 | 1.47 |
| Total | 100.00 | 99.20 |

A cumulative and sequential use of microwave-assisted extractions, combined to a judicious use of an appropriate solvent provides an extract in greater yield than conventional steam distillation products (0.94%) alone. Also, the extract is of higher commercial market value and reduces the quantity of solvent, another desirable factor. Furthermore, the time required to reduce and/or evaporate the extract to dryness is reduced to one-third. The latter enhances the efficiency of the process and reduces costs associated with manpower and energy consumption; in fact, reduction and/or evaporation of the solvent is the rate-determining step of this microwave-assisted extraction process. In the above example, three complete extracts are produced within ten minutes, whereas the same extract would have required a minimum of eight hours by conventional steam distillation processes.

EXAMPLE 6

Intact garlic cloves having a 30% moisture content were immersed in 250 mL of dichloromethane. The immersed samples were then irradiated with microwave radiation at 625 Watts and a frequency 2,450 MHz for a single 30-second exposure period. The samples, being completely intact in this Example, illustrated exemplary constituent extraction with no contamination of the extracted constituents with less desirable constituents. Yields were found were to 22.2% for diallyl sulfide, 28.4% for 3-vinyl-1,2 dithi-5-ene and 49.4% for 2-vinyl-1,3 dithi-4-ene. The analysis of the products produced by the process herein is identified as $\mu$-wave$_2$.

TABLE VI

| Constituent | GARLIC CONSTITUENTS | | | | |
|---|---|---|---|---|---|
| | $HD_1$ | $HD_2$ | $CO_2$ | $\mu$-wave$_1$ | $\mu$-wave$_2$ |
| Allyl methyl sulfide | — | — | — | 1.23 | — |
| Dimethyl sulfide | — | — | 1.41 | — | — |
| Diallyl sulfide | 1.33 | 3.89 | — | — | — |
| Allyl methyl disulfide | 3.05 | 5.32 | 5.58 | 8.12 | — |
| Methyl prop-1-enyl disulfide | — | — | — | 5.41 | — |
| Methyl prop-2-enyl disulfide | — | 1.26 | — | — | — |
| Dimethyl trisulfide | — | — | — | 1.12 | — |
| Diallyl disulfide | 31.2 | 30.7 | 16.7 | 17.7 | 22.2 |
| Dipropenyl disulfide | 1.38 | 1.83 | — | — | — |
| Diprop-2-enyl disulfide | 4.76 | 6.88 | 1.41 | — | — |
| Allyl methyl trisulfide | 11.2 | 12.4 | — | 7.38 | — |
| 3-vinyl-1,2-dithi-5-ene | — | — | 23.3 | 4.47 | 28.4 |
| 2-vinyl-1,3-dithi-4-ene | 1.84 | — | 46.5 | 34.3 | 49.4 |
| Diallyl trisulfide | 33.8 | 22.4 | — | — | — |
| Dipropenyl trisulfide | — | — | — | 2.29 | — |
| Diallyl tetrasulfide | 1.04 | — | — | — | — |
| Dipropenyl tetrasulfide | 4.24 | 1.32 | — | — | — |

$HD_1$ denotes hydrodiffusion; $HD_2$ denotes hydrodistillation; $CO_2$ denotes supercritical fluid extraction with $CO_2$; $\mu$-wave$_1$ denotes macerated garlic in dichloromethane with 4 irradiations of 125 seconds; $\mu$-wave$_2$ denotes intact garlic cloves in dichloromethane and irradiated for a single 30-second microwave irradiation period.

The data clearly illustrate that even under brief exposure time (30 seconds) coupled with a cool medium for the extraction of the constituents, the technique of the present invention greatly exceeds the conventional techniques of hydrodiffusion, hydrodistillation, supercritical fluid extraction and, more importantly, microwave extraction where the sample was macerated and over exposed to microwave energy.

EXAMPLE 7

A fresh rainbow trout (*Salmo qalrdneri*) was provided and the pectoral fins, together with the dorsal fin and the head, were removed to form a source material for a first extraction (38.5g). From the same fish, the complete internal parts were separated to provide a source material for a second extraction (34.9g).

Each of these source materials were then subjected to a sequential series of microwave extractions (3×15 seconds) using the same extractant, according to the present invention. The apparatus employed was that described in Example 1; the extractant employed for each source material was hexane (a single 60 ml aliquot) which immersed the materials completely. It is important to note that the source materials were in a non-particulated state. In addition, the temperature of the extractant remained at a point where the extractant functioned to cool the expressed oil from these source materials.

The oils expressed from the starting materials were then separated from the hexane by procedures described in the other Examples and the recovered products were analyzed for their fatty acid contents.

As reported in the Agricultural Handbook 8-15 (U.S. Department of Agriculture, 1987), pressing of rainbow trout to separate essential oils from edible parts yields, by conventional techniques, a total of about 3.4% of free lipids. In general terms, such pressing techniques require a significant amount of time, which by comparison to the techniques of the present invention, represent several times that of the microwave extraction technique herein. In addition, the percentage yield using the process of the present invention, for the essential oils, and using only trout fins and a small content of flesh as source material, is somewhat larger (3.9%) to the yields by conventional techniques when using whole edible fish parts. Furthermore, using the fish internal parts with the present invention, approximately five-fold (16.1 vs. 3.4%) increase in the amount of essential oils was obtained compared to the conventional pressing techniques.

DETAILED DESCRIPTION OF THE PREFERRED EMBODIMENTS

Referring now to FIG. 1, shown is the apparatus of the present invention having a reservoir or tank 10 with an inlet 11 for the biological material and an inlet 12 for the solvent previously discussed, which may be stored in solvent reservoir 13. Feeding the solvent into the tank 10 is controlled by valve 14. The mixture of solvent and biological material is stirred by a stirrer 15. A pump 16 feeds mixed solvent and plant material through a microwave applicator 17, (consisting of one or several sources) with a typical power rating of about 200 to about 10,000 Watts and a typical operating frequency of between 2,000 to about 30,000 MHz. Further, pump 18 feeds the treated material and solvent to a filtering apparatus 19. Also, a microwave source could be positioned within the supply tubing to enclose it within the feed material tube. The microwaves act directly on the cellular material to disrupt the same subsequently releasing the oils or other substances into the extractant for cooling thereby.

A plurality of filters used with or without desiccants may be provided in the filtering apparatus, acting in parallel. This enables filtered residual biological solids to be removed periodically from individual filters, without shutting down the apparatus completely.

From the filtering apparatus 19, the filtered solvent and oils therein are pumped, by pump 20, to a separator 21 or recycled to the microwave applicator 17 via valves 51 and 52 and tube 50. Separator 21 is heated, as by external heater 22, controlled by a temperature controller 23, to evaporate the solvent. The remaining substance or substances in the separator 21 is drawn off periodically at outlet 24 controlled by valve 25.

Evaporated solvent is passed through a condenser 26, and condensed solvent is fed back into a main reservoir 27 where it is then fed to the solvent reservoir 13, controlled by valve 28. In a modification, the condensed solvent could be fed directly to the solvent reservoir 13.

Some of the condensed solvent can be diverted through the filter 19 to increase the extraction in the filter. This is provided by pipe 30, controlled by valves 31 and 32. Various relief valves are provided, as at 33 and 34, for opening the apparatus to atmospheric pressure.

As described previously herein, the apparatus is for obtaining volatile oils and other substances by the use of microwaves to disrupt the glandular cells containing such oils. The apparatus can be combined with other conventional forms of apparatus. For example, a distribution valve 40 is provided between the microwave applicator 17 and the filter apparatus 19. From the valve, depending upon its setting, the mixed biological material and solvent can be fed to the filtering apparatus 19, as described above, or fed via a connection 41 to a conventional steam distillation plant. With such an application, the solvent is water and the mixed biological material and water can be treated in the microwave applicator, the water being heated. Alternatively, the water can be heated by the microwave applicator 17 until it reaches the vapour phase, under pressure, and is allowed to condense via connection 41, through the biological material that would be placed into the steam distillation reservoir (hydrodistillation and hydrodiffusion).

In another alternative, valve 40 can be set to permit flow through a connection 42 to a solids/liquid extraction plant. The mixed plant material and solvent may or may not be treated in the microwave applicator for the duration of the initial fill-up reflux sequence. The reflux of this operation could be returned directly to pump 16 for subsequent operations.

A particularly preferred form of the apparatus described above is utilized in conjunction with a supercritical fluid extraction process wherein the microwave applicator utilizes a system of tubing, such as glass, quartz or the like connected to or enclosed within an outer tubing of metal such as steel and in which the microwave apparatus uses an axially positioned microwave generating means within the tube and through which the material to be irradiated flows. In this way, a continuous process with its advantages can be utilized. Still further, other arrangements may be employed where the microwave generating means may be positioned surrounding a microwave transparent tube or conduit and in which the generating means is shielded by suitable material e.g. metal. In such a case, the transparent conduit material can be Teflon (TM) or glass.

For improved operation, it may be desirable to operate the system under vacuum conditions. More particularly, solvent removal by evaporation is greatly facilitated by reducing the pressure while maintaining a relatively low temperature. Connections at 43 and 44 provide for connection to a vacuum source.

The apparatus provides for increased extraction of certain essences and other substances which must be removed, or are preferably removed, without the application of heat, as by heating with a solvent.

Although specific embodiments of the present invention have been described above, it is not limited thereto and it will be apparent to those skilled in the art that numerous modifications form part of the present invention insofar as they do not depart from the spirit, nature and scope for the claimed and described invention.

I claim:

1. A process for extracting soluble products including volatile oils from biological material comprising:
   (b) contacting the sub-divided material with a non-aqueous extractant which is transparent or partially transparent to microwave radiation;
   (c) exposing the sub-divided material while in contact with sufficient extractant to enable extraction to occur, to a microwave energy source to effect differential heating between said biological material and said non-aqueous extractant to thereby express said volatile oils from said biological material and immediately cooling the expressed volatile oils from said biological material with said non-aqueous extractant to a temperature below the temperature at which the expressed volatile oils are extracted from the biological material; and
   (d) separating the residual material from the extractant phase.

2. The process of claim 1 wherein the biological material is plant tissue.

3. The process of claim 1 wherein the biological material has a dispersed moisture content which is within about 25 to about 90% by weight.

4. The process of claim 1 wherein the biological material is subdivided sufficiently that all of the desired soluble products are accessible to the extractant.

5. The process of claim 1 wherein the extractant is partially transparent to microwave and part of the extractant is impregnated into the material to become a dispersed component having a microwave absorption, before step (c).

6. The process of claim 1 wherein the biological material contains desired labile or volatile components and the extractant is selected to be sufficiently transparent to the applied microwave radiation that the labile or volatile components will be extracted.

7. The process of claim 1 wherein the biological material contains undesired labile or volatile soluble components and the extractant is selected from those partially transparent to the microwave so that sufficient heating due to microwave absorption will occur to drive off or decompose aid undesired components.

8. The process of claim 1 wherein the residual material after step (d) is contacted with a second extractant having different solvent or penetration characteristics than the first, and exposed to microwave radiation a second time to generate a second extraction product.

9. The process of claim 1 wherein the ratio (L/kg) of the extractant to said subdivided material ranges from about 1:1 to about 20:1.

10. The process of claim 1 wherein the microwave radiation exposure has a duration of from about 10 to about 100 seconds at a power of about 200 to about 10,000 watts and a frequency of 2000–20,000 MHz, and the dose is selected to enhance the extraction.

11. The process of claim 1 wherein, as a further step (e), the extracted product is recovered from the extractant phase and the depleted extractant phase is recycled to step (b).

12. The process of claim 1 wherein the biological feed material is in dry condition and is hydrated or rehydrated with moisture prior to step (c).

* * * * *

UNITED STATES PATENT AND TRADEMARK OFFICE
CERTIFICATE OF CORRECTION

PATENT NO. : 5,338,557
DATED : August 16, 1994
INVENTOR(S) : J.R. Jocelyn Paré

It is certified that error appears in the above-indentified patent and that said Letters Patent is hereby corrected as shown below:

Column 15, claim 1, at line 2, after "comprising" insert,

-- (a) sub-dividing a biological feed material into sub-divided material; --

Signed and Sealed this

Twenty-ninth Day of November, 1994

Attest:

BRUCE LEHMAN

*Attesting Officer*  *Commissioner of Patents and Trademarks*